United States Patent [19]

Smith

[11] Patent Number: 5,552,320
[45] Date of Patent: Sep. 3, 1996

[54] SELF-CONTAINED BIOLOGICAL INDICATOR

[75] Inventor: Daniel F. Smith, Irvine, Calif.

[73] Assignee: Johnson & Johnson Medical, Inc., Arlington, Tex.

[21] Appl. No.: 406,262

[22] Filed: Mar. 16, 1995

Related U.S. Application Data

[63] Continuation of Ser. No. 103,875, Aug. 9, 1993, abandoned.

[51] Int. Cl.$^6$ ................................................ C12M 1/40
[52] U.S. Cl. .................. 435/287.4; 435/31; 435/262; 435/287.6; 435/288.2; 422/28; 422/30; 422/58; 422/61
[58] Field of Search ............... 435/29, 31, 287, 435/288, 286, 262, 287.4, 288.2, 287.6; 422/28, 30, 58, 61

[56] References Cited

U.S. PATENT DOCUMENTS

| | | | |
|---|---|---|---|
| 3,239,429 | 3/1966 | Menolasino et al. | 195/54 |
| 3,346,464 | 10/1967 | Ernst | 195/54 |
| 3,440,144 | 4/1969 | Andersen | 195/103.5 |
| 3,661,717 | 5/1972 | Nelson | 195/103.5 R |
| 3,711,378 | 1/1973 | Kereluk | 195/103.5 R |
| 3,752,743 | 8/1973 | Henshilwood | 195/127 |
| 3,846,242 | 11/1974 | Ernst . | |
| 3,991,881 | 11/1976 | Augurt | 206/439 |
| 4,071,412 | 1/1978 | Eisenberg et al. | 195/102 |
| 4,087,326 | 5/1978 | Kereluk | 195/103.5 R |
| 4,291,122 | 9/1981 | Orelski | 435/31 |
| 4,311,793 | 1/1982 | Halleck | 435/31 |
| 4,328,182 | 5/1982 | Blake | 422/56 |
| 4,348,209 | 9/1982 | Murtaugh et al. | 23/232 R |
| 4,416,984 | 11/1983 | Wheeler, Jr. | 435/31 |
| 4,448,548 | 5/1984 | Foley | 374/31 |
| 4,461,837 | 7/1984 | Karle et al. | 435/296 |
| 4,528,268 | 7/1985 | Andersen et al. | 435/31 |
| 4,569,913 | 2/1986 | Koths | 435/190 |
| 4,579,823 | 4/1986 | Ryder | 435/296 |
| 4,580,682 | 4/1986 | Gorski et al. | 206/569 |
| 4,591,566 | 5/1986 | Smith | 435/291 |
| 4,636,472 | 1/1987 | Bruso | 435/287 |
| 4,671,936 | 6/1987 | Barron | 422/55 |
| 4,717,661 | 1/1988 | McCormick et al. | 435/31 |
| 4,829,001 | 5/1989 | Menke et al. | 435/264 |
| 4,943,414 | 7/1990 | Jacobs et al. | 422/28 |
| 5,073,488 | 12/1991 | Matner et al. | 435/31 |
| 5,223,401 | 6/1993 | Foltz et al. | 435/18 |
| 5,486,459 | 1/1996 | Burnhom et al. | 435/31 |

FOREIGN PATENT DOCUMENTS

| | | |
|---|---|---|
| 105747 | 4/1984 | European Pat. Off. . |
| 421760 | 4/1991 | European Pat. Off. . |
| 2251069 | 6/1992 | United Kingdom . |

OTHER PUBLICATIONS

Wallen et al J Food Science vol. 44 No. 2 (1979) pp. 560–563.

Primary Examiner—Esther M. Kepplinger
Assistant Examiner—Milton I. Cano
Attorney, Agent, or Firm—James Riesenfeld; Andrew C. Farmer

[57] ABSTRACT

A self-contained biological indicator includes an outer container that is translucent and liquid impermeable. The container is normally closed by a vapor-permeable, microorganism-impermeable closure and contains a source of viable microorganisms, a culture medium, a composition that decomposes hydrogen peroxide, and a detector that undergoes a visible change in response to growth of the microorganisms. In operation, the indicator is first subjected to a sterilization cycle in a hydrogen peroxide sterilizer. Without opening the outer container, the microorganism source, culture medium, and hydrogen peroxide-decomposing composition are brought into contact. The indicator is placed in an incubator, after which the detector responds to any microorganism growth, indicative of incomplete sterilization. But for the hydrogen peroxide-decomposing composition, hydrogen peroxide that becomes bound to the microorganism support during sterilization, could kill the microorganisms afterwards, yielding a false indication of complete sterilization.

10 Claims, 2 Drawing Sheets

SELF-CONTAINED BIOLOGICAL INDICATOR

This a continuation of application Ser. No. 08/103,875, filed Aug. 9, 1993 now abandoned.

BACKGROUND OF THE INVENTION

1. Field of the Invention

This invention relates to a biological indicator, more specifically to a self-contained biological indicator for a hydrogen peroxide sterilizer or a hydrogen peroxide plasma sterilizer.

2. Description of the Related Art

Biological indicators (or "sterility indicators") are devices that are used to test the efficacy of sterilizers, such as those that are commonly used in hospitals for sterilizing medical instruments, glassware, etc. The indicators include a source of microorganisms, a culture medium, and a detector to indicate the presence or absence of viable microorganisms. The culture medium may also serve as the detector, with formation of a cloudy suspension indicating growth of microorganisms. In practice, the source of microorganisms, typically an absorbent paper strip that has been impregnated with a predetermined concentration of live microorganisms, is subjected to a sterilization process. Thereafter, the microorganism impregnated strip is placed in a sterile culture medium and incubated for a predetermined time at an appropriate temperature. At the end of the incubation period, the detector is used to determine whether any microorganisms survived the sterilization process. In some indicators, microorganism survival, which means the sterilization was incomplete, is shown by a change in color of the detector.

To simplify the sterilization test process and minimize the risk that external contamination would affect the test results, the elements of the biological indicator—microorganisms, culture medium, and detector—have sometimes been packaged in a way that permits the microorganism source, culture, and indicator to be combined without exposing the biological indicator to the non-sterile surroundings. A number of these so-called "self-contained biological indicators" (SCBI) have been described in the patent literature.

U.S. Pat. No. 3,440,144, issued Apr. 22, 1969, to H. W. Anderson discloses an SCBI that includes a heat-sealed bag which contains a sterilized culture medium in a closed ampule and source of bacterial spores on a piece of absorbent paper. The ampule has a spout that can easily be broken without removing the ampule from the bag. The bag is placed in a sterilizer along with items to be sterilized. After the sterilization is complete, the spout is broken off and the culture medium contacts the absorbent paper. The still-sealed bag is then placed in an incubator for a predetermined time, sufficient to permit any surviving spores to give a visual indication.

U.S. Pat. No. 3,661,717 issued May 9, 1972, to Robert L. Nelson, discloses an SCBI in which the culture medium is contained in an inner compartment that is in snug engagement with an outer compartment that also contains viable microorganisms and a detector that changes color in response to growth of the microorganism. The "snug engagement" minimizes voids in which sterilizing gases can be trapped. Release of the trapped gas after completion of the sterilization cycle can result in a false indication of sterility.

A number of later patents disclose refinements that purport to provide SCBI's that are easier to use, provide results more quickly, and/or give more accurate results (see, e.g., U.S. Pat. Nos. 4,416,984; 4,580,682; 4,717,661; 5,073,488; and 5,223,401).

These references all have in common the fact that they are adapted for use with traditional sterilizers, such as those that use steam, radiation, or ethylene oxide. A type of sterilizer that has a number of advantages over these traditional sterilizers is the hydrogen peroxide plasma sterilizer that is disclosed in U.S. Pat. No. 4,643,876, issued Feb. 17, 1987, to Paul T. Jacobs et al. This sterilizer combines the use of hydrogen peroxide and plasma to provide a sterilizer that avoids undesirable characteristics of earlier sterilizers that exposed devices to be sterilized, and, potentially, workers as well, to high temperatures, high levels of radiation, or toxic gases. Sterilizers that use hydrogen peroxide alone, without plasma, are also available. In this specification and the appended claims, we use "hydrogen peroxide sterilizers" to refer to both types of sterilizers.

A sterilizer test pack for use with hydrogen peroxide sterilizers is disclosed in European Patent Application 90310824.9, published Apr. 10, 1991. That reference does not disclose details of an SCBI that would be suitable for use with that type of sterilizer.

Hydrogen peroxide is commonly used to protect food from spoilage by inhibiting microorganism growth. In order to assess the effectiveness of hydrogen peroxide for that purpose, it may be important to measure the recovery of spores damaged by hydrogen peroxide. S. E. Wallen and H. W. Walker evaluated media and procedures for spore recovery (J. of Food Science 44,560 (1979)). They used a phosphate buffer containing catalase to decompose the hydrogen peroxide, after the spores were exposed to the hydrogen peroxide for a predetermined time. Hydrogen peroxide is also known to be a cleaning and disinfecting agent for hygienic articles, such as contact lenses. U.S. Pat. Nos. 4,585,488 and 4,748,992, issued to G. Giefer on Apr. 29, 1986 and June 7, 1988, respectively, disclose a system for cleaning and disinfecting contact lenses that includes disinfecting the lenses with a hydrogen peroxide disinfection solution and then decomposing residual hydrogen peroxide with an aqueous solution of a decomposition catalyst comprising dissolved catalase. Others have also addressed the problem of neutralizing hydrogen peroxide residues on contact lenses. Representative of these are U.S. Pat. No. 4,899,914; European Patent Application 86308559.3; Canadian Patent 1,297,403; and PCT Applications WO 86/07264; WO 91/12825; and WO 92/11041.

SUMMARY OF THE INVENTION

In accordance with the present invention, a sterility indicator for a hydrogen peroxide sterilizer comprises a translucent, liquid impermeable outer container, having an opening that is normally closed by a vapor-permeable, microorganism-impermeable closure, and containing a) a source of viable microorganisms, b) at least one closed inner container containing a liquid culture medium that, with incubation, is capable of promoting growth of the viable microorganisms and a composition that is capable of decomposing hydrogen peroxide, c) means actuable externally to the outer container for opening the at least one closed inner container to permit the source of microorganisms, culture medium, and hydrogen peroxide-decomposing composition to be brought into contact, and d) a detector contained in at least one of the containers and capable of undergoing a visible change in response to growth of the microorganism.

The indicator provides an accurate test of the operation of a hydrogen-peroxide sterilizer, without requiring a great deal of skill and care by the operator.

DETAILED DESCRIPTION OF THE INVENTION

A variety of types of sterilizers are used to sterilize medical devices, but the types most commonly used in hospitals and other medical facilities are those that use as the sterilant either steam or gas (ethylene oxide). A number of self-contained biological indicators (SCBI's) are commercially available for testing the operation of these sterilizers. Among these are Attest™ indicators (3M) for monitoring steam sterilizers, EZ Test indicators (SGM Biotech) for monitoring ethylene oxide sterilizers, and Proof Plus® indicators (AMSCO) for monitoring both steam and ethylene oxide sterilizers.

These commercial SCBI's generally include an absorbent paper strip that has been impregnated with spores or other viable microorganisms. The criterion for determining whether the sterilizer is operating satisfactorily is whether subjecting the SCBI's to a sterilization cycle causes all the microorganisms on the strip to be destroyed. In principle, these SCBI's could be used with a hydrogen peroxide sterilizer, such as the Sterrad™ hydrogen peroxide plasma sterilization system (Johnson & Johnson Medical, Inc.). However, these commercial SCBI's could potentially indicate falsely that a hydrogen peroxide sterilizer was operating satisfactorily. That could happen by the following mechanism. During the sterilization cycle, hydrogen peroxide is bound (by absorption, for example) to the paper that supports the spores. At the end of the cycle, viable spores may remain, which indicates the sterilization was incomplete—but these spores could be killed by the subsequent release of absorbed hydrogensperoxide. Thus, when the culture medium is added and the strip is incubated, there would be no growth of microorganisms.

The SCBI of the present invention overcomes that drawback of prior art indicators by including in the SCBI a catalyst that neutralizes residual hydrogen peroxide. Thus, if viable microorganisms survive the sterilization procedure, they will grow in the culture medium when incubated and they will be detected. The hydrogen peroxide is typically neutralized by decomposing it to water and oxygen. In this specification and the appended claims, "neutralize" and "decompose" are used interchangeably to refer to the process by which the hydrogen peroxide is inactivated.

Figure 1:
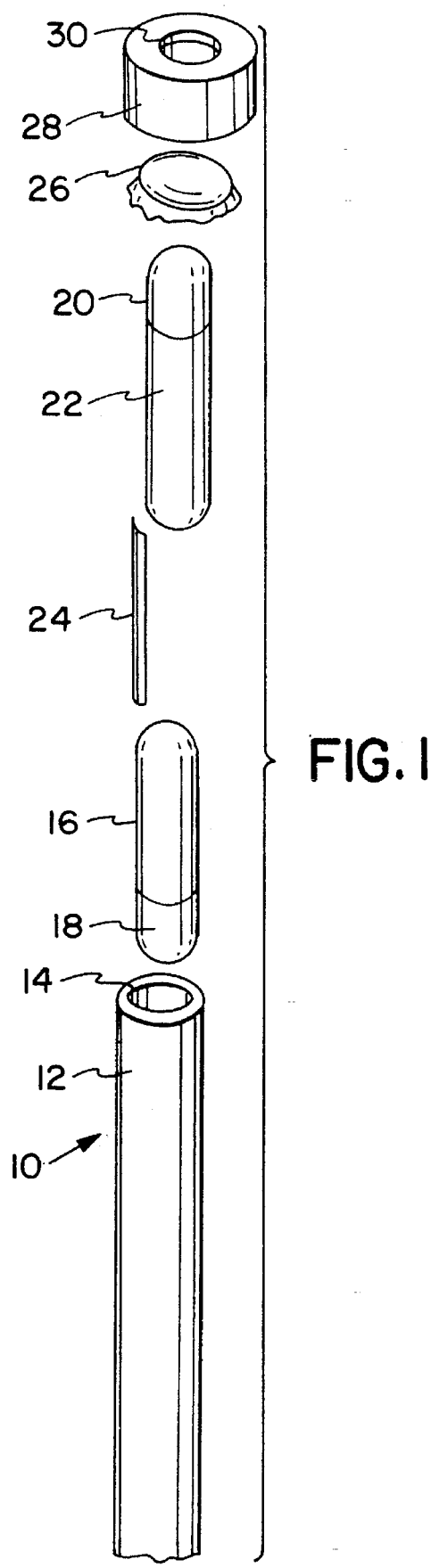
FIG. 1 is an exploded perspective view of a sterility indicator of the present invention.

FIG. 1 depicts an exploded perspective view of a sterility indicator of the present invention, whose structure is similar to that of the SCBI described in U.S. Pat. No. 3,661,717. Translucent outer container 10 has liquid impermeable walls 12 and open end 14. Closed inner container 16 contains a composition 18 that can neutralize hydrogen peroxide. Closed inner container 20 contains a liquid culture medium 22. Filter paper 24 is impregnated with a predetermined concentration of viable spores or other microorganisms. Outer container 10 is closed by vapor-permeable, microorganism-impermeable closure sheet 26, which is held in place by cap 28, which has an aperture 30.

Either or both containers 16 and 20 also contain a detector that undergoes a visible change in response to growth of the microorganisms. The visible change should be detectable without the need to breach outer container 10, which requires that container 10 have walls that are translucent. As used in the present specification and claims, "translucent" is the quality of the container walls that permits visible changes to be detected from the outside. Thus, for example, transparent walls would clearly be included. In the embodiment shown in FIG. 1, containers 16 and 20 are of a frangible material, such as glass, and walls 12 of container 10 are deformable to permit the inner container to be opened (by crushing, for example), without breaking the walls of outer container 10. However, any other suitable construction of SCBI's, well known in the art, may also be used. Closure sheet 26 may be a nonwoven fabric, such as Tyvek® or any other suitable material.

Although shown in FIG. 1 to be in separate containers 16 and 20, the liquid culture medium and hydrogen peroxide neutralizing composition could both be in a single container. Composition 18 could be any of a number of compositions known in the art as being suitable for decomposing hydrogen peroxide, including catalase, peroxidase, and other peroxide-neutralizing catalysts. A preferred composition is catalase, more preferably freeze-dried catalase powder. The catalase powder is preferably mixed with a stabilizer powder, such as a sugar, a salt, other stabilizers well known in the art, or combinations thereof. The stabilizer not only extends the shelf life of the catalyst but also increases the quantity of powder to be used. This is desirable, since very little pure catalase would be needed for a single SCBI. The stabilizer mustn't interfere with growth of the microorganism.

Metal catalysts, such as platinum, palladium, iron, etc, are also suitable, provided they don't inhibit the growth of the microorganisms. Since high surface area is desirable, the preferred form of the metal catalyst is either a fine powder of the metal or a coating of the metal on a fine ceramic powder.

Figure 2:
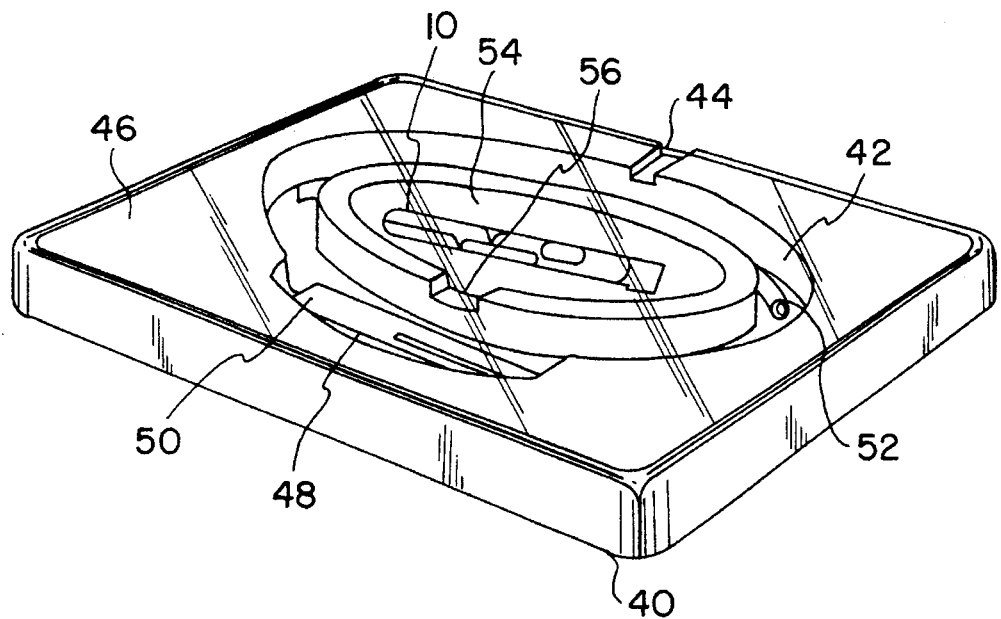
FIG. 2 is a front-top view of a test pack that includes a sterility indicator of the present invention.
Figure 3:
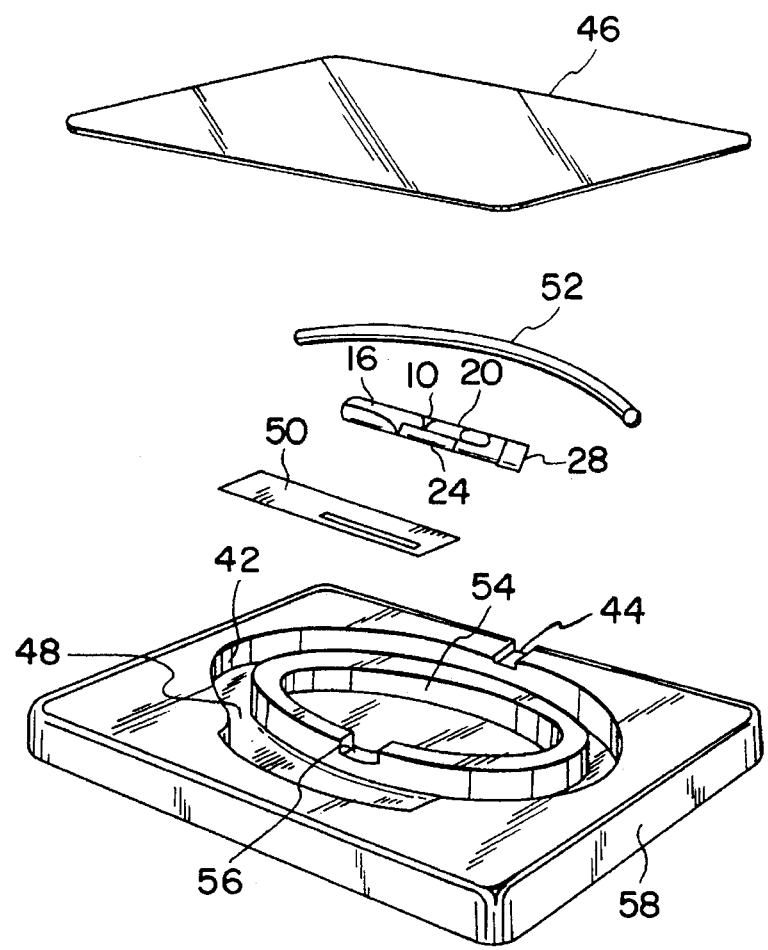
FIG. 3 is an exploded view of the test pack of FIG. 2

When a load of articles is placed into a sterilizer to be sterilized, some articles typically have less direct access to the sterilant than others. A sterility indicator should test the sterilizer's operation with respect to articles having the least access to the sterilant. Thus, although the SCBI of this invention, whose exploded view is shown in FIG. 1, can be used alone, it is generally desirable to incorporate the SCBI in a "test pack." The purpose of the test pack is to impede access of the hydrogen peroxide sterilant to the SCBI, thereby simulating the most difficult to reach objects of a sterilizer load. FIGS. 2 and 3 depict an SCBI of the present invention in a test pack. The pack has a bottom tray 40 made of thermoformable material such as polycarbonate, polyethylene, polypropylene, polystyrene, PVC, acrylic plastics or polyester. The base is formed with an oval annular passage 42. Passage 42 communicates with the atmosphere outside through opening 44 defined by trays. 40 and peelable top 46. Tray 40 further defines a space 48 which receives a chemical indicator strip 50.

Strip 50 is provided with a chemical which changes color when exposed to the hydrogen peroxide sterilization atmosphere.

Within oval passage 42 but opposite chemical indicator strip 50 is an absorber 52. This provides a load to retard the passage of the atmosphere from outside the package. Absorber 52 may be made of any convenient substance which absorbs the hydrogen peroxide atmosphere, such as paper, rubber, nylon, polyurethane or PVC. Rubber tubing is preferred.

Tray 40 defines a blind reservoir 54 which communicates with passage 42 via connecting opening 56. Reservoir 54 contains the SCBI of FIG. 1. Peelable top 46 is made of a clear plastic film or foil. Although a clear polyester is used in the preferred embodiment, polycarbonate, polyethylene polypropylene, polystyrene, PVC, acrylic plastics, nylon or an opaque aluminum foil may be used.

The top 46 is held in place by a suitable adhesive. The adhesive preferably seals the top 46 to tray 40. One corner may be left without adhesive near the corner portion to permit ease of grasping top 46 to separate it from tray 40 for access to the indicators.

The tray 40 has a depending skirt 58 to prevent curling of the corners. The tray is thermoformed and receives absorber 52, chemical indicator strip 50, and the SCBI. The peelable top is then sealed to the upper surface of tray 40, so that the only communication between passage 42 and the outside is through opening 44.

In use, the test pack is placed within the chamber of a sterilizer along with the objects to be sterilized. During the operation of the sterilizer, a portion of the atmosphere enters passage 42 through opening 44. Absorber 52 retards the hydrogen peroxide sterilant from traveling around to the chemical indicator strip 50. As the process continues, the sterilant permeates past absorber 52 and around to strip 50 causing the strip to indicate it has been in contact with the sterilant. As the sterilization process continues, a portion of the hydrogen peroxide permeates through connecting opening 56 and into the blind reservoir 54 where it acts on the SCBI.

After being subjected to a sterilization cycle, either alone or as part of a test pack, the SCBI is then removed promptly, and the inner containers (or container) are promptly opened to cause contact among the source of microorganisms, the culture medium, the hydrogen peroxide-decomposing composition, and the detector. (Promptness is dictated by the need to combine the elements of the SCBI before any substantial additional killing of the microorganisms takes place.) The SCBI is then placed in a conventional incubator at a temperature and for a time suitable for growing the microorganism in the culture medium. For exmaple, if the microorganism is a spore strip inoculated with *B. subtilis* var niger spores and the culture medium is Tryptic Soy Broth (available from SGM Biotech, Bozeman, Mont.), then incubation should take place for about 48 hours at 37° C. When the detector is phenol red, microbial growth produces acid that turns the color to yellow, which indicates that sterilization was not complete. The absence of a color change confirms that sterilization conditions were achieved.

I claim:

1. A sterility indicator for use with a hydrogen peroxide sterilizer, said sterility indicator comprising a translucent, liquid impermeable outer container, having an opening that is normally closed by a vapor-permeable, microorganism-impermeable closure, and containing:
   a) a source of viable microorganisms,
   b) at least one closed inner container containing a liquid culture medium that, with incubation, is capable of promoting growth of the viable microorganisms and an agent for decomposing hydrogen peroxide,
   c) opening means actuable external to the outer container for opening the at least one closed inner container to permit the source of microorganisms, culture medium, and hydrogen peroxide-decomposing composition to be brought into contact, and
   d) a detector means contained in at least one of the containers for undergoing a visible change in response to growth of the microorganisms;

whereby the sterility indicator may be subjected to a hydrogen peroxide based sterilization procedure in a hydrogen peroxide sterilizer, and whereafter said opening means may be actuated to bring the source of microorganisms, culture medium, and hydrogen peroxide-decomposing composition into contact with one another and with the detector means, and whereby the agent for decomposing hydrogen peroxide will decompose any hydrogen peroxide left in the sterility indicator after said sterilization procedure, and whereafter if any of the microorganisms remain viable they will grow in said culture medium and said detector means will provide a visual indication that said sterilization procedure failed to sterilize all of said microorganisms.

2. The sterility indicator of claim 1 in which the source of viable microorganisms comprises an absorbent strip inoculated with spores.

3. The sterility indicator of claim 1 wherein the at least one closed inner container comprises a first closed inner container which contains the liquid culture medium and a second closed inner container which contains the agent.

4. The sterility indicator of claim 1 wherein the agent comprises catalase.

5. The sterility indicator of claim 4 wherein the catalase comprises freeze dried catalase powder.

6. The sterility indicator of claim 1 wherein the agent comprises a metal catalyst.

7. The sterility indicator of claim 6 wherein the metal is selected from the group consisting of platinum, palladium and iron.

8. The sterility indicator of claim 1 wherein the opening means comprises the at least one inner container being frangible.

9. The sterility indicator of claim 8 wherein the opening means further comprises the outer container being flexible.

10. A test pack for use with a hydrogen peroxide sterilizer comprising:
    a) a housing having an inner volume and a first opening for communication between the inner volume and the outside of the housing; and
    b) a divider that divides the inner volume into two sections that communicate through a second opening,
       i) a first section that is between the opening and a blind reservoir and that contains a hydrogen peroxide absorber and a chemical indicator responsive, visually to contact with hydrogen peroxide and
       ii) a second section that is the blind reservoir and that contains a sterility indicator of claim 1.

* * * * *